US006630473B1

United States Patent
Waki

(10) Patent No.: US 6,630,473 B1
(45) Date of Patent: Oct. 7, 2003

(54) ANTI-INFLAMMATORY AGENTS AND INHIBITORS AGAINST INCREASE IN OCULAR TENSION CAUSED BY IRRADIATION WITH LASERS, CONTAINING 1,4-DIHYDROPYRIDINE DERIVATIVES

(75) Inventor: Mitsunori Waki, Kobe (JP)

(73) Assignees: Senju Pharmaceutical Co., Ltd., Osaka (JP); Kyoto Pharmaceutical Industries, Ltd., Kyoto (JP)

( * ) Notice: Subject to any disclaimer, the term of this patent is extended or adjusted under 35 U.S.C. 154(b) by 0 days.

(21) Appl. No.: 09/890,354
(22) PCT Filed: Jan. 27, 2000
(86) PCT No.: PCT/JP00/00410
§ 371 (c)(1), (2), (4) Date: Oct. 10, 2001
(87) PCT Pub. No.: WO00/44383
PCT Pub. Date: Aug. 3, 2000

(30) Foreign Application Priority Data

Jan. 29, 1999 (JP) .......................................... 11-022249

(51) Int. Cl.[7] ...................... A61K 31/496; A61P 27/00; C07D 211/90
(52) U.S. Cl. .................. 514/253.13; 514/341
(58) Field of Search ............................ 514/253.13, 341

(56) References Cited

U.S. PATENT DOCUMENTS

| 4,937,242 A | 6/1990 | Matsui et al. ............. 514/235.8 |
| 5,435,998 A | 7/1995 | Abelson ................... 424/78.04 |

FOREIGN PATENT DOCUMENTS

| EP | 0 968 716 | | 1/2000 |
| JP | 63-225355 | * | 9/1988 |
| JP | 3-145464 | * | 3/1991 |
| JP | 03-145464 | | 6/1991 |
| JP | 3-145464 | | 6/1991 |
| JP | 4-244081 | * | 4/1992 |
| JP | 4-244081 | | 9/1992 |
| JP | 04-244081 | | 9/1992 |
| JP | 63-225355 | | 9/1998 |
| WO | 98/18471 | | 5/1998 |
| WO | WO 98/18471 | * | 7/1998 |

OTHER PUBLICATIONS

Chem. Abstract 131:39685.*
Yoshihiro Kaji et al., "The effects of calcium antagonists on prostaglandin $E_2$ reaction in rabbit eyes", Journal of Japanese Ophthalmological Society, 98, pp. 825–831, (1994).
Yoshihiro Kaji et al., "Inhibitory effect of calcium antagonist on intraocular inflammation", Abstracts of the 60th Annual Meeting of MID–Japan Ophthalmological Society, p. 134, (1994).
Miyoko Ota, "Effects of a new topical calcium channel blocker after endothelin–1 injection into the vitreous body rabbits", Journal of Osaka Ika Daigaku, vol. 57, No. 3, pp. 50–57, (1999).
Y. Kaji et al., "Nicardipine inhibits acute rise of aqueous flare and intraocular pressure induced by argon laser photocoagulation", Ocular Immunology and Inflammation, 4, pp. 139–144, (1996).
C. Kadoi et al., "Sites of disruption of the blood–aqueous barrier after application of prostaglandin $E_2$ in pigmented rabbits", Ophthalmic Research, 29, pp. 365–373, (1996).
X. Zhang et al., "Nilvadipine inhibits acute rise of aqueous flare and intraocular pressure induced by prostaglandin $E_2$ in pigmented rabbits", Ophthalmic Research, 30, pp. 135–141, (1998).
"Calcium Channel Blockers in the Management of Low–tension and Open–Angle Glaucoma", Netland et al., Am. J. Opthalmology 115: 608, 1993.
Miyoko Ota, "Endotheline–1 katogan junkai shogai model no VEP ni taisuru atarashii $Ca^{2+}$ kikkoyaku tengan no koka", Journal of Osaka Ika Daigaku, vol. 57, No. 3, pp. 50–57, (1999) & Chemical Abstracts, 131:39685.

* cited by examiner

Primary Examiner—Mukund J. Shah
Assistant Examiner—Harry Liu
(74) Attorney, Agent, or Firm—Wenderoth, Lind & Ponack, L.L.P.

(57) ABSTRACT

The present invention provides an anti-inflammatory medicament and an inhibitor of intraocular pressure rise due to laser irradiation, which contains 1,4-dihydropyridine derivative of the formula (I)

(I)

wherein $X^1$ and $X^2$ are the same or different and each is hydrogen atom, fluoromethyl, fluoromethoxy, halogen, cyano or nitro, $R^1$ is lower alkyl, $R^2$ is acyl, alkoxycarbonyl, acylalkyl, N-alkyl-substituted carbamoylalkyl, alkoxyalkyl, alkoxycarbonylalkyl, acyloxyalkyl, nitratoalkyl, cyanoalkyl, hetero ring-alkyl, haloalkyl, alkenyl or alkynyl, A is alkylene having a carbon atom bonded with two alkyls and 5 or more carbon atoms in total, and m is an integer of 1 to 3, or an acid addition salt thereof, as an active ingredient.

9 Claims, No Drawings

ANTI-INFLAMMATORY AGENTS AND INHIBITORS AGAINST INCREASE IN OCULAR TENSION CAUSED BY IRRADIATION WITH LASERS, CONTAINING 1,4-DIHYDROPYRIDINE DERIVATIVES

TECHNICAL FIELD

The present invention relates to anti-inflammatory medicaments and inhibitors against increase in ocular tension caused by irradiation with lasers, which contain a specific 1,4-dihydropyridine derivative or an acid addition salt thereof.

BACKGROUND ART

While the administration of prostaglandin $E_2$ ($PGE_2$) via cornea induces inflammatory responses in the anterior uveal tissues and a temporary rise of intraocular pressure, it is known that systemic administration of a dihydropyridine Ca antagonist, nicardipine, [(Yoshihiro KAJI, Shigeyoshi HIRAKI and Hideki HIRATA: Effect of calcium antagonist on ophthalmic inflammatory response by exogenous prostaglandin $E_2$, Journal of Japanese Ophthalmological society, 98: 825–831, 1994), (Yoshihiro KAJI, Shigeyoshi HIRAKI, Hideki HIRATA and Seiji HAYASAKA: Nicardipine inhibits acute rise of aqueous flare and intraocular pressure induced by argon laser photocoagulation, Ocular Immunol. Inflam., 4: 139–144, 1996)], nilvadipine [(Chiharu KADOI, Shigeyoshi HIRAKI, Seiji HAYASAKA and Osamu OHOTANI: Sites of disruption of the blood-aqueous barrier after application of prostaglandin $E_2$ in pigmented rabbits, Ophthalmic Research 29: 365–373, 1996), (Xue-Yun ZHANG, Shigeyoshi HIRAKI and Seiji HAYASAKA: Nilvadipine inhibits acute rise of aqueous flare and intraocular pressure induced by prostaglandin $E_2$ in pigmented rabbits, Ophthalmic Research 30: 135–141, 1998)] or Ca-antagonist, felodipine (Shigeyoshi HIRAKI, Xue-Yun ZHANG, Tomohiro ABE, Seiji HAYASAKA: Inhibitory effect of Ca Antagonist Felodipine on Experimental Endophthalmitis, 17th Japan Ophthalmic Pharmacological Convention, 1997, 7., Morioka) before administration of $PGE_2$ inhibits these responses in a dose-dependent manner. Furthermore, while the argon laser is used for ophthalmic operation of angle-closure glaucoma, retinal detachment and the like, intravenous administration of Nicardipine has been reported to have inhibited experimental endophthalmitis induced by photocoagulation of iris by the argon laser (Yoshihiro KAJI, Shigeyoshi HIRAKI and Hideki HIRATA et al.: inhibitory, effect of calcium antagonist on intraocular inflammation, Abstracts of the 60th Annual Meeting of MID-Japan Ophthalmological Society, 134, 1994). It has been also reported that felodipine has an inhibitory effect on experimental endophthalmitis induced by photocoagulation of iris by the argon laser and LPS endophthalmitis induced by systemic administration of endotoxin (lipopolysaccharide=LPS) [Yoshihiro KAJI, Xue-Yun ZHANG and Seiji HAYASAKA: Inhibitory Effect of Felodipine (Ca-antagonist) on Experimental Endophthalmitis of House Rabbit, Abstracts of the 18th Annual Meeting of the Japanese ophthalmo-Pharmacological Society, 56–57, 1998].

It is already known that a certain kind of Ca antagonist, 1,4-dihydropyridine derivative and an acid addition salt thereof, are useful as a hypotensive medicament, a therapeutic medicament of angina pectoris, a cerebral circulation improving medicament, a peripheral circulation improving medicament, a renal function improving medicament, an anti-arterial sclerosis medicament, a smooth muscle relaxant, an antiallergic medicament, a therapeutic medicament of cataract, a therapeutic medicament of glaucoma (JP-A-63-225355) and an ophthalmic circulation disorder improving medicament (PCT/JP97/03866).

The 1,4-dihydropyridine derivative of the following formula (I) and an acid addition salt thereof are known to have various uses mentioned above. However, an anti-inflammatory effect and an inhibitory effect on the rise of intraocular pressure due to laser irradiation, particularly, an inhibitory effect on intraocular inflammation and rise of intraocular pressure due to laser irradiation, which is provided by topical administration of these compounds to the eye, has not been known yet.

DISCLOSURE OF THE INVENTION

Under the circumstances, the present inventor has closely studied the efficacy of the Ca antagonist, 1,4-dihydropyridine derivative and an acid addition salt thereof to be mentioned later, and found that these compounds have a superior anti-inflammatory effect and an inhibitory effect on the rise of intraocular pressure due to laser irradiation, and further studies have resulted in the completion of the present invention.

It is therefore an object of the present invention to provide a novel pharmaceutical use of a 1,4-dihydropyridine derivative or an acid addition salt thereof. More particularly, the present invention provides an anti-inflammatory medicament and an inhibitor of intraocular pressure rise due to laser irradiation, which contain a 1,4-dihydropyridine derivative or an acid addition salt thereof.

Accordingly, the present invention provides the following.

(1) An anti-inflammatory medicament containing, as an active ingredient, a 1,4-dihydropyridine derivative of the formula (I)

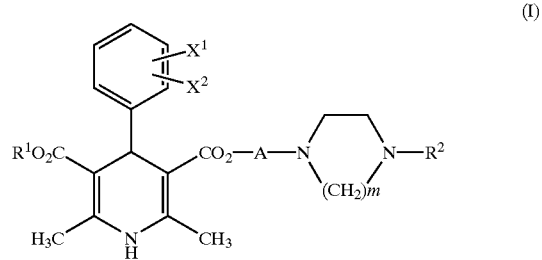

wherein $X^1$ and $X^2$ are the same or different and each is hydrogen atom, fluoromethyl, fluoromethoxy, halogen, cyano or nitro, $R^1$ is lower alkyl, $R^2$ is acyl, alkoxycarbonyl, acylalkyl, N-alkyl-substituted carbamoylalkyl, alkoxyalkyl, alkoxycarbonylalkyl, acyloxyalkyl, nitratoalkyl, cyanoalkyl, hetero ring-alkyl, haloalkyl, alkenyl or alkynyl, A is alkylene having a carbon atom bonded with two alkyls and 5 or more carbon atoms in total, and m is an integer of 1 to 3, or an acid addition salt thereof (hereinafter sometimes to be referred as an inventive compound).

(2) The anti-inflammatory medicament of the above-mentioned (1), wherein, in the formula (I), $R^2$ is acylalkyl, N-alkyl-substituted carbamoylalkyl, alkoxyalkyl, cyanoalkyl, hetero ring-alkyl, haloalkyl, alkenyl or alkynyl.

(3) The anti-inflammatory medicament of the above-mentioned (1), wherein, in the formula (I), $R^2$ is alkenyl or alkynyl.

(4) The anti-inflammatory medicament of the above-mentioned (1), wherein, in the formula (I), A is alkylene having a carbon atom bonded with two alkyls and 5 to 10 carbon atoms in total.
(5) The anti-inflammatory medicament of the above-mentioned (1), wherein the acid addition salt of the 1,4-dihydropyridine derivative of the formula (I) is 3-(4-allyl-1-piperazinyl)-2,2-dimethylpropyl methyl 2,6-dimethyl-4-(m-nitrophenyl)-1,4-dihydropyridine-3,5-dicarboxylate dihydrochloride.
(6) The anti-inflammatory medicament of any of the above-mentioned (1) to (5), wherein the objective disease is intraocular inflammation.
(7) The anti-inflammatory medicament of the above-mentioned (6), wherein the intraocular inflammation is caused by laser irradiation.
(8) The anti-inflammatory medicament of the above-mentioned (6) or (7), Which is for a topical administration to the eye.
(9) The anti-inflammatory medicament of the above-mentioned (8), which is in the form of an eye drop.
(10) The anti-inflammatory medicament of the above-mentioned (8), which is in the form of an eye ointment.
(11) An inhibitor of intraocular pressure rise due to laser irradiation, which contains, as an active ingredient, a 1,4-dihydropyridine derivative of the formula (I)

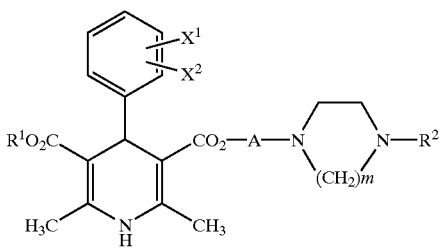

(I)

wherein $X^1$ and $X^2$ are the same or different and each is hydrogen atom, fluoromethyl, fluoromethoxy, halogen, cyano or nitro, $R^1$ is lower alkyl, $R^2$ is acyl, alkoxycarbonyl, acylalkyl, N-alkyl-substituted carbamoylalkyl, alkoxyalkyl, alkoxycarbonylalkyl, acyloxyalkyl, nitratoalkyl, cyanoalkyl, hetero ring-alkyl, haloalkyl, alkenyl or alkynyl, A is alkylene having a carbon atom bonded with two alkyls and 5 or more carbon atoms in total, and m is an integer of 1 to 3, or an acid addition salt thereof.
(12) The inhibitor of intraocular pressure rise due to laser irradiation of the above-mentioned (11), wherein, in the formula (I), $R^2$ is acylalkyl, N-alkyl-substituted carbamoylalkyl, alkoxyalkyl, cyanoalkyl, hetero ring-alkyl, haloalkyl, alkenyl or alkynyl.
(13) The inhibitor of intraocular pressure rise due to laser irradiation of the above-mentioned (11), wherein, in the formula (I), $R^2$ is alkenyl or alkynyl.
(14) The inhibitor of intraocular pressure rise due to laser irradiation of the above-mentioned (11), wherein, in the formula (I), A is alkylene having a carbon atom bonded with two alkyls and 5 to 10 carbon atoms in total.
(15) The inhibitor of intraocular pressure rise due to laser irradiation of the above-mentioned (11), wherein the acid addition salt of the 1,4-dihydropyridine derivative of the formula (I) is 3-(4-allyl-1-piperazinyl)-2,2-dimethylpropyl methyl 2,6-dimethyl-4-(m-nitrophenyl)-1,4-dihydropyridine-3,5-dicarboxylate dihydrochloride.
(16) The inhibitor of intraocular pressure rise due to laser irradiation of any of the above-mentioned (11) to (15), which is for a topical administration to the eye.
(17) The inhibitor of intraocular pressure rise due to laser irradiation of the above-mentioned (16), which is in the form of an eye drop.
(18) The inhibitor of intraocular pressure rise due to laser irradiation of the above-mentioned (16), which is in the form of an eye ointment.
(19) A method for preventing or treating inflammation, which method comprises administering an effective amount of the 1,4-dihydropyridine derivative of the formula (I) or an acid addition salt thereof of the above-mentioned (1).
(20) A method for inhibiting rise of intraocular pressure due to laser irradiation, which method comprises administering an effective amount of the 1,4-dihydropyridine derivative of the formula (I) or an acid addition salt thereof of the above-mentioned (11).
(21) Use of the 1,4-dihydropyridine derivative of the formula (I) or an acidaddition salt thereof of the above-mentioned (1) for the production of an anti-inflammatory medicament.
(22) Use of the 1,4-dihydropyridine derivative of the formula (I) or an acid addition salt thereof of the above-mentioned (11) for the production of an inhibitor of intraocular pressure rise due to laser irradiation.
(23) A pharmaceutical composition for preventing or treating inflammation, which composition contains the 1,4-dihydropyridine derivative of the formula (I) or an acid addition salt thereof of the above-mentioned (1), and a pharmaceutically acceptable carrier.
(24) A pharmaceutical composition for inhibiting rise of intraocular pressure due to laser irradiation, which composition contains the 1,4-dihydropyridine derivative of the formula (I) or an acid addition salt thereof of the above-mentioned (11) and a pharmaceutically acceptable carrier.
(25) A commercial package comprising a pharmaceutical composition of the above-mentioned (23) and a written matter associated therewith, the written matter stating that the pharmaceutical composition can or should be used for preventing or treating inflammation.
(26) A commercial package comprising a pharmaceutical composition of the above-mentioned (24) and a written matter associated therewith, the written matter stating that the pharmaceutical composition can or should be used for inhibiting rise of intraocular pressure due to laser irradiation.

BRIEF DESCRIPTION OF THE DRAWINGS

FIG. 1 is a graph showing an inhibitory effect on the rise of the intraocular pressure (IOP) after laser irradiation, by intravenous administration of nicardipine hydrochloride, wherein the axis of abscissas shows time (hr), the axis of ordinates shows the intraocular pressure (IOP), a white circle means intravenous administration of nicardipine hydrochloride, a black circle means control without administration and each value shows mean±standard error (n=4) where significant difference from control: *;$p<0.05$, ;$p<0.01$, *;$p<0.001$.

FIG. 2 is a graph showing an inhibitory effect on the rise of the intraocular pressure (IOP) after laser irradiation, by instillation of 0.1% iganidipine hydrochloride, wherein the axis of abscissas shows time (hr) and the axis of ordinates shows the intraocular pressure (IOP). In the graph of treated eye, a white circle means instillation of iganidipine hydrochloride and a black circle means control with administration of physiological saline, and in the graph of non-treated eye, a white circle means instillation of physiological saline into the opposite eye from the eye instilled with iganidipine hydrochloride, a black circle means control without administration to the opposite eye from the eye instilled with physiological saline, and each value shows mean±standard error (n=4) where significant difference from control: *;$p<0.05$, ;$p<0.01$, *;$p<0.001$.

FIG. 3 is a graph showing an inhibitory effect on the rise of the intraocular pressure (IOP) after laser irradiation, by instillation of 0.05% iganidipine hydrochloride, wherein the axis of abscissas shows time (hr) and the axis of ordinates shows the intraocular pressure (IOP). In the graph of treated eye, a white circle means instillation of iganidipine hydrochloride and a black circle means control with administration of physiological saline, and in the graph of non-treated eye, a white circle means instillation of physiological saline into the opposite eye from the eye instilled with iganidipine hydrochloride, a black circle means control without administration to the opposite eye from the eye instilled with physiological saline, and each value shows mean±standard error (n=4) where significant difference from control: *;$p<0.05$, ;$p<0.01$, *;$p<0.001$.

FIG. 4 is a graph showing an inhibitory effect on the rise of the intraocular pressure (IOP) after laser irradiation, by instillation of 0.1% nicardipine hydrochloride, wherein the axis of abscissas shows time (hr) and the axis of ordinates shows the intraocular pressure (IOP). In the graph of treated eye, a white circle means instillation of nicardipine hydrochloride and a black circle means control with administration of physiological saline, and in the graph of non-treated eye, a white circle means instillation of physiological saline into the opposite eye from the eye instilled with nicardipine hydrochloride, a black circle means control without any administration to the opposite eye from the eye instilled with physiological saline, and each value shows mean±standard error (n=4) where significant difference from control: *;$p<0.05$, ;$p<0.01$, *;$p<0.001$.

DETAILED DESCRIPTION OF THE INVENTION

In the present specification, $C_x$ means that the number of carbon atoms is X. For example, $C_{1-4}$ means that the number of carbon atoms is 1 to 4.

The anti-inflammatory medicament and the inhibitor of intraocular pressure rise due to laser irradiation of the present invention contain the 1,4-dihydropyridine derivative of the formula (I) (hereinafter to be also referred to as 1,4-dihydropyridine derivative (I)) or an acid addition salt thereof as an active ingredient.

In the formula (I), fluoromethyl at $X^1$ and $X^2$ is monofluoromethyl, difluoromethyl or trifluoromethyl, fluoromethoxy is monofluoromethoxy, difluoromethoxy or trifluoromethoxy, and halogen means fluorine atom, chlorine atom, bromine atom or iodine atom.

In the formula (I), the lower alkyl at $R^1$ preferably has 1 to 4 carbon atoms, and may be linear, branched or cyclic. Examples thereof include methyl, ethyl, n-propyl, isopropyl, n-butyl, isobutyl, sec-butyl, tert-butyl, cyclopropylmethyl and the like.

In the formula (I), acyl at $R^2$ may be any of aliphatic acyl, aromatic acyl, heterocyclic acyl. The aliphatic acyl preferably has 1 to 5 carbon atoms, and may be linear or branched and saturated or unsaturated. When it is unsaturated, it preferably has 1 or 2 double bond(s) or triple bond(s). The aromatic acyl or heterocyclic acyl may be that wherein a carbonyl group is directly bonded to an aromatic group or a heterocyclic group or that wherein a carbonyl group is bonded to an aromatic group via an aliphatic group (e.g., saturated or unsaturated and having 1 to 3 carbon atoms, and when it is unsaturated, it has 1 or 2 double bond(s) or triple bond(s)). The hetero ring is preferably a 5- or 6-membered ring, particularly that wherein the hetero atom is a nitrogen atom or an oxygen atom. The aliphatic group, aromatic group and hetero group of aliphatic acyl, aromatic acyl and heterocyclic acyl may be substituted by halogen (chlorine atom, bromine atom and the like), hydroxyl group, carboxyl group, alkoxyl group, acyl group, acylamino group and the like.

Preferable examples of acyl group at $R^2$ include formyl, acetyl, crotonoyl, acryloyl, propioloyl, benzoyl, phenylacetyl, cinnamoyl, p-acetamino benzoyl, m-methoxybenzoyl, m-dimethylamino benzoyl, p-hydroxycinnamoyl, furoyl, nicotinoyl, piperidinomethylcarbonyl and the like.

The alkoxycarbonyl at $R^2$ is that having linear or branched $C_{1-5}$ alkoxy. Preferable examples include methoxycarbonyl, ethoxycarbonyl, propoxycarbonyl, tert-butoxycarbonyl and the like.

The acyl of acylalkyl at $R^2$ is exemplified by those mentioned above and alkyl is exemplified by linear or branched $C_{1-5}$ alkyl. Preferable examples include phenacyl, acetonyl, methylcarbonylethyl, pyrrolidinocarbonylmethyl and the like.

The N-alkyl-substituted carbamoylalkyl at $R^2$ may be mono-substituted or di-substituted. AS the alkyl group of the substituent, linear or branched $C_{1-5}$ alkyl is exemplified. Preferable examples include methylcarbamoylmethyl, piperadinocarbamoylmethyl, dimethylcarbamoylmethyl and the like.

The alkoxy and alkyl of alkoxyalkyl at $R^2$ are exemplified by linear or branched $C_{1-5}$ alkoxy and $C_{1-5}$ alkyl. Preferable examples include methoxyethyl, ethoxyethyl, methoxypropyl and the like.

The alkoxy and alkyl of alkoxycarbonylalkyl at $R^2$ are exemplified by linear or branched $C_{1-5}$ alkoxy and $C_{1-5}$ alkyl. Preferable examples include methoxycarbonylmethyl, ethoxycarbonylmethyl, ethoxycarbonylethyl and the like.

The acyl of acyloxyalkyl at $R^2$ is exemplified by those mentioned above, and as the alkyl, linear or branched $C_{1-5}$ alkyl is exemplified. Preferable examples include acetoxyethyl, benzoyloxyethyl and the like.

The alkyl of nitratoalkyl at $R^2$ is exemplified by linear or branched $C_{1-5}$ alkyl. Preferable examples include nitratoethyl, nitratopropyl and the like.

The alkyl of cyanoalkyl at $R^2$ is exemplified by linear or branched $C_{1-5}$ alkyl. Preferable examples include cyanomethyl, cyanoethyl and the.like.

The hetero ring of hetero ring-alkyl at $R^2$ is preferably exemplified by 5- or 6-membered ring, which particularly has a nitrogen atom or oxygen atom as the hetero atom. Examples thereof include piperidino, morpholino and the like. As the alkyl, linear or branched $C_{1-5}$ alkyl is exemplified. Preferable examples include piperidinoethyl, morpholinoethyl and the like.

The halogen of haloalkyl at $R^2$ is exemplified by fluorine atom, chlorine atom, bromine atom and the like, and as the alkyl, linear or branched $C_{1-5}$ alkyl is exemplified. Preferable examples include halogen-trisubstituted methyl (e.g., trifluoromethyl), halogen-monosubstituted ethyl (e.g., monofluoroethyl) and the like.

As the alkenyl and alkynyl at $R^2$ are exemplified by linear or branched $C_{2-5}$ alkenyl and $C_{2-5}$ alkynyl, such as vinyl, propenyl, isopropenyl, butenyl, ethynyl, propinyl, butynyl, pentinyl and the like.

In the formula (I), alkylene having a carbon atom bonded with two alkyls and 5 or more carbon atoms in total, which is represented by A, may be linear or branched, and preferably has 10 or less, particularly 8 or less, carbon atoms. Examples thereof include 2,2-dimethyltetramethylene, 2,2-dimethylpentamethylene, 2,2-dimethylhexamethylene, 2,2-dimethyltrimethylene, 1,1-dimethyltrimethylene and the like, with preference given to 2,2-dimethyltrimethylene.

In the formula (I), m is preferably 1 or 2.

The 1,4-dihydropyridine derivative of the formula (I) wherein $R^2$ is acylalkyl, N-alkyl-substituted carbamoylalkyl, alkoxyalkyl, cyanoalkyl, hetero ring-alkyl, haloalkyl, alkenyl or alkynyl (particularly, $R^2$ is alkenyl or alkynyl), and an acid addition salt thereof are particularly superior in pharmacological action and water solubility.

The acid addition salt of 1,4-dihydropyridine derivative (I) includes, for example, inorganic salts such as hydrochloride, sulfate, hydrogen bromide and phosphate, and organic salts such as acetate, succinate, maleate, fumarate, malate, tartrate and methanesulfonate, and may be any as long as it is pharmacologically acceptable.

Examples of the 1,4-dihydropyridine derivative (I) to be contained in the anti-inflammatory medicament and inhibitor of intraocular pressure rise due to laser irradiation of the present invention include the following compounds.

(1) 3-(4-allyl-1-piperazinyl)-2,2-dimethylpropyl methyl 2,6-dimethyl-4-(m-nitrophenyl)-1,4-dihydropyridine-3,5-dicarboxylate dihydrochloride [general name: iganidipine hydrochloride]

(2) 3-[4-(2-propenyl)-1-piperazinyl]-2,2-dimethylpropyl methyl 2,6-dimethyl-4-(m-nitrophenyl)-1,4-dihydropyridine-3,5-dicarboxylate dihydrochloride (3) 3-(4-cyanomethyl-1-piperazinyl)-2,2-dimethylpropyl methyl 2,6-dimethyl-4-(m-nitrophenyl)-1,4-dihydropyridine-3,5-dicarboxylate dihydrochloride (4) 3-[4-(2-methyl-2-propenyl)-1-homopiperazinyl]-2,2-dimethylpropyl methyl 2,6-dimethyl-4-(m-nitrophenyl)-1,4-dihydropyridine-3,5-dicarboxylate dihydrochloride (5) 3-(4-allyl-1-homopiperazinyl)-2,2-dimethylpropyl methyl 2,6-dimethyl-4-(m-nitrophenyl)-1,4-dihydropyridine-3,5-dicarboxylate dihydrochloride (6) 3-[4-(tert-butyloxycarbonyl)-1-homopiperazinyl]-2,2-dimethylpropyl methyl 2,6-dimethyl-4-(m-nitrophenyl)-1,4-dihydropyridine-3,5-dicarboxylate (7) 3-(4-formyl-1-homopiperazinyl)-2,2-dimethylpropyl methyl 2,6-dimethyl-4-(m-nitrophenyl)-1,4-dihydropyridine-3,5-dicarboxylate The 1,4-dihydropyridine derivative (I) and an acid addition salt thereof of the present invention can be appropriately synthesized according to the method described in the above-mentioned JP-A-63-225355 and a method analogous thereto.

The 1,4-dihydropyridine derivative (I) and an acid addition salt thereof of the present invention are useful for the prophylaxis and/or treatment of inflammation in mammals.

In addition, the 1,4-dihydropyridine derivative (I) and an acid addition salt thereof of the present invention are useful for the inhibition of rise of intraocular pressure in mammals due to laser irradiation.

The above-mentioned mammals are exemplified by human, cattle, horse, dog, rabbit, mouse, rat and the like.

The objective disease of the anti-inflammatory medicament of the present invention includes, for example, hemorrhoid, arthritis rheumatoides, rheumatoides deformans, osteoarthritis of spine, arthrosis deformans, lumbar pain, gouty attack, acute middle otitis, cystitis, prostatitis, dental pain, inflammatory paranasal sinus and the like. The intraocular inflammation, which is the object of the anti-inflammatory medicament of the present invention, includes uveitis, Harada's disease, Behcet disease, iridocyclitis, conjunctivitis, blepharitis ciliaris, optic neuritis, keratitis, scleritis, dacryocystitis and intraocular inflammation induced by laser irradiation.

The inhibitor of intraocular pressure rise due to laser irradiation of the present invention can be advantageously used for inhibiting the rise of intraocular pressure associated with laser irradiation during ophthalmic laser operation of, for example, angle-closure glaucoma and retinal detachment.

When this compound is used as an anti-inflammatory medicament and an inhibitor of intraocular pressure rise due to laser irradiation, one or more kinds of the inventive compounds can be used in a suitable combination depending on the object and need thereof.

The 1,4-dihydropyridine derivative (I) and an acid addition salt thereof can be administered orally or parenterally as an anti-inflammatory medicament and an inhibitor of intraocular pressure rise due to laser irradiation. The dosage form of the preparation includes, for example, solid preparation such as tablet, granule, powder, capsule, ointment (particularly eye ointment) and the like, liquid preparation such as injection and eye drop, which can be prepared by a known method. These preparations may contain various additives for general use, such as carrier, excipient, binder, thickener, dispersing agent, re-absorption enhancer, buffer, surfactant, solubilizer, preservative, emulsifier, isotonic agent, stabilizer, pH adjusting agent and the like.

When this preparation is used for inhibiting intraocular inflammation and the rise of intraocular pressure due to laser irradiation, the preparation is preferably administered topically to the eye, more preferably in the form of an eye drop or an eye ointment, for the prevention of side effects and the like.

The additives used for an eye drop are exemplified by the following.

As the buffer, for example, phosphate, borate, citrate, tartarate, acetate, amino acid and the like are used (preferably buffer having buffering capacity at pH 2–9). The isotonic agent includes, for example,. saccharides such as sorbitol, glucose, mannitol and the like, polyhydric alcohols such as glycerin, polyethylene glycol, propylene glycol and the like, salts such as sodium chloride and the like. The preservative includes, for example, benzalkonium chloride, benzetonium chloride, paraoxybenzoates such as methyl paraoxybenzoate, ethyl paraoxybenzoate and the like, benzyl alcohol, phenethyl alcohol, sorbic acid and salts thereof, thimerosal, chlorobutanol and the like. Examples of the thickener include hydroxyethylcellulose, hydroxypropylcellulose, methylcellulose, hydroxypropylmethylcellulose, carboxymethylcellulose, salts thereof and the like. As the solubilizer (stabilizer), used are water soluble polymers such as cyclodextrins, polyvinylpyrrolidone and the like, surfactants such as polysorbate 80 and the like, and the like. Examples of the chelating agent include sodium edetate, sodium citrate, condensed sodium phosphate and the like. Examples of the suspending agent include surfactants such as polysorbate 80 and the like, and water soluble polymers such as sodium methylcellulose, hydroxypropylmethylcellulose, methylcellulose and the like.

For the eye ointment, an ointment base material such as petrolatum, lanoline and the like can be used.

When the inventive compound is used as an anti-inflammatory medicament or an inhibitor of intraocular pressure rise due to laser irradiation, the dose is about 1 mg—about 100 mg for an adult in the case of an injection, about 10 mg—about 1000 mg for an adult in the case of oral administration given several times a day, though subject to change depending on the kind of the compound to be used, the kind of the objective disease, the age and body weight of patients, applicable diseases, dosage form and the like. When it is used as an eye drop, an eye drop having a concentration of about 0.001 (w/v)%—about 5 (w/v)% is instilled several times a day by several drops per instillation for an adult, when it is used as an eye ointment, an eye ointment having a concentration of about 0.001 (w/w)%—about 5 (w/w)% is administered several times a day to an adult.

The anti-inflammatory medicament and the inhibitor of intraocular pressure rise due to laser irradiation of the present invention may contain other anti-inflammatory medicaments, intraocular pressure rise inhibitors and other kinds of suitable efficacious ingredients, as long as the object of the present invention is not impaired.

EXAMPLES

The present invention is explained in more detail in the following by referring to Examples and Formulation Examples. The scope of the present invention is not limited by these examples.

Example 1

Effect of the inventive compound on intraocular inflammation and rise of intraocular pressure due to argon laser irradiation The effect of the inventive compound on intraocular inflammation and rise of intraocular pressure induced by photocoagulation of iris due to argon laser irradiation was examined. As regards intraocular inflammation, the anterior chamber protein concentration (photon/msec) was used as an index.

Test Material

An eye drop of the inventive compound, 3-(4-allyl-1-piperazinyl)-2,2-dimethylpropyl methyl 2,6-dimethyl-4-(m-nitrophenyl)-1,4-dihydropyridine-3,5-dicarboxylate dihydrochloride [general name: iganidipine chloride], was prepared according to the following formulation at a concentration of 0.05% and 0.1% and at pH 5.

As a control substance, 0.1% nicardipine chloride, perdipine [trademark] Injections, Yamanouchi Pharmaceutical Co., Ltd., was used.

| | |
|---|---|
| iganidipine hydrochloride | 0.1, 0.05 g |
| sodium acetate | 0.1 g |
| sodium chloride | 0.9 g |
| benzalkonium chloride | 0.005 g |
| acetic acid | appropriate amount |
| distilled water | total amount 100 ml |

Test Animal

Male Dutch colored house rabbits weighing about 2 kg purchased from Fukusaki Rabbit Breeding Cooperative were used for the test, after confirmation of absence of abnormality. The rabbits were raised at temperature of 23±3° C., humidity of 55±10% on a solid feed (the NOSAN GROUP: Labo R Stock, NIHON NOSAN) 100 g a day, allowing free access to tap water.

Test Method

The intraocular pressure was measured in advance using a pneumatonograph (Alcon) at 30 minutes and immediately before instillation, and house rabbits that showed stable intraocular pressure were selected. The argon laser was irradiated in the middle of both eyes between limbus and the base of iris at 5 sites at the same intervals, under the conditions of size: 200 $\mu$m, irradiation time (duration): 0.5 sec, output (power): 0.35 W. To remove the effect of fibrin that occurs after laser irradiation, heparin (1000 U/kg) was intravenously administered.

The increase in the anterior chamber protein concentration caused by ophthalmic inflammation was measured with a laser flare cell meter (Kowa Co., Ltd.) immediately before, 30 minutes after and 1 hour after laser irradiation.

The intraocular pressure of the both eyes was measured immediately before and 0.25, 0.5, 1, 2, 3 and 4 hours after laser irradiation.

(1) Intravenous Administration of Nicardipine Hydrochloride

Nicardipine hydrochloride was intravenously administered at 30 minutes and immediately before laser irradiation by 500 $\mu$g/500 $\mu$l/kg. Heparin was administered 5 minutes after the first administration of nicardipine hydrochloride. Heparin was administered to the control group at 30 minutes before laser irradiation.

(2) Instillation of Iganidipine Hydrochloride and Nicardipine Hydrochloride

Into one eye of the house rabbits was instilled 0.05% and 0.1% iganidipine hydrochloride and 0.1% nicardipine hydrochloride, and into each opposite eye was instilled physiological saline by 10 $\mu$l at 30 minutes before laser irradiation. The eye instilled with the test material was taken as the treated eye, and the opposite eye instilled with physiological saline was taken as the non-treated eye. In view of the influence of the test material on the opposite eye, the control eyes were prepared, wherein physiological saline was instilled into one eye, and the other eye was not treated, respectively taken as the control of the treated eye and the control of the non-treated eye. Heparin was intravenously administered immediately after instillation of the test material and physiological saline.

Results

The results are shown in Table 1–Table 4 and FIG. 1–FIG. 4.

TABLE 1

Effect on protein concentration (/msec) by intravenous administration of nicardipine hydrochloride after laser irradiation

| Time (min) | control | nicardipine hydrochloride |
|---|---|---|
| 0 | 12.85 ± 1.87 | 15.53 ± 0.14 |
| 30 | 182.05 ± 14.70 | 58.08 ± 18.14* |
| 60 | 336.20 ± 37.23 | 30.85 ± 2.58* |

Each value shows mean ± standard error (n = 4).
significant difference from control group *;p < 0.001.

TABLE 2

Effect on protein concentration (/msec) by instillation of 0.1% iganidipine hydrochloride after laser irradiation

| Time (min) | Treated eye | | Non-treated eye | |
|---|---|---|---|---|
| | control | iganidipine hydrochloride | control | iganidipine hydrochloride |
| 0 | 12.85 ± 1.87 | 19.18 ± 2.37 | 11.68 ± 0.66 | 16.03 ± 2.97 |
| 30 | 182.05 ± 14.70 | 84.70 ± 29.66* | 199.78 ± 48.48 | 117.33 ± 31.50 |
| 60 | 336.20 ± 37.23 | 227.18 ± 10.03 | 320.83 ± 19.49 | 244.45 ± 39.46 |

Each value shows mean ± standard error (n = 4).
significant difference from conrol group *;$p < 0.05$.

TABLE 3

Effect on protein concentration (/msec) by instillation of 0.05% iganidipine hydrochloride after laser irradiation

| Time (min) | Treated eye | | Non-treated eye | |
|---|---|---|---|---|
| | control | iganidipine hydrochloride | control | iganidipine hydrochloride |
| 0 | 12.85 ± 1.87 | 20.55 ± 5.02 | 11.68 ± 0.66 | 11.73 ± 2.97 |
| 30 | 182.05 ± 14.70 | 73.75 ± 8.67* | 199.78 ± 48.48 | 68.53 ± 14.40 |
| 60 | 336.20 ± 37.23 | 284.10 ± 17.03 | 320.83 ± 19.49 | 313.13 ± 27.06 |

Each value shows mean ± standard error (n = 4).
significant difference from control group *;$p < 0.001$.

TABLE 4

Effect on protein concentration (/msec) by instillation of 0.1% nicardipine hydrochloride after laser irradiation

| Time (min) | Treated eye | | Non-treated eye | |
|---|---|---|---|---|
| | control | nicardipine hydrochloride | control | nicardipine hydrochloride |
| 0 | 12.85 ± 1.87 | 20.55 ± 5.02 | 11.68 ± 0.66 | 11.73 ± 2.97 |
| 30 | 182.05 ± 14.70 | 184.05 ± 35.1 | 199.78 ± 48.48 | 118.93 ± 21.21 |
| 60 | 336.20 ± 37.23 | 337.23 ± 46.4 | 320.83 ± 19.49 | 349.85 ± 23.02 |

Each value shows mean ± standard error (n = 4).

As is evident from Table 1, anterior chamber protein concentration at 30 minutes after laser irradiation was 182.1/msec for the control group and 58.1/msec for the nicardipine hydrochloride intravenous administration group, thus significantly inhibiting the protein concentration. As shown in the earlier report, (Abstracts of the 60th Annual Meeting of MID-Japan Ophthalmological Society, 134, 1994 mentioned above), nicardipine hydrochloride was confirmed to significantly inhibit protein concentration by intravenous administration.

FIG. 1 clearly shows that the control group showed the maximum intraocular pressure of 42.1 mmHg at 30 minutes after laser irradiation, which was higher than the initial value by 16.4 mmHg, and showed gradual decrease thereafter. At 2 hours after the irradiation, the intraocular pressure returned to the original level, and 4 hours later, decreased by 7 mmHg from the initial value. In contrast, the nicardipine hydrochloride intravenous administration group showed the intraocular pressure of 30.1 mmHg immediately before laser irradiation, 24.2 mmHg at 30 minutes after the irradiation, and 20.8 mmHg at 1 hour after the irradiation, showing a decrease by 9.3 mmHg, and the effect was sustained until 4 hours after the irradiation, thus showing significant inhibition of the rise of intraocular pressure.

As Tables 2–4 clearly show, the anterior chamber protein concentration varied in the control group shown in the above-mentioned (1) (i.e., the eye instilled with physiological saline which is the control group of the treated eyes in Tables 2–4), whereas the anterior chamber protein concentration of the eye instilled with 0.1% iganidipine hydrochloride at 30 minutes after laser irradiation was 84.7/msec, and that of the eye instilled with 0.05% iganidipine hydrochloride was 73.8/msec, thus showing significant inhibition. However, the eye instilled with 0.1% nicardipine hydrochloride showed the concentration of 184.1/msec, without difference from the control group. With any test material, the protein concentration did not vary in the opposite eye, which was instilled with physiological saline (i.e., the eye group instilled with each test material of the non-treated eyes in Tables 2–4). As shown, the inventive compound effectively inhibited an increase in the anterior chamber protein concentration that rose due to the laser irradiation, and found to be useful for intraocular inflammation.

As FIGS. 2–4 clearly show, the increase in the intraocular pressure was significantly inhibited with only the rise by 7.5 mmHg from the initial value at 30 minutes from laser irradiation in the eye instilled with 0.1% iganidipine hydrochloride, and that by 6 mmHg from the initial value in the eye instilled with 0.05% iganidipine hydrochloride. The intraocular pressure decreased thereafter, and restored to the original intraocular pressure in 2 hours with 0.1% iganidipine hydrochloride, and 90 minutes by the administration of 0.05% iganidipine hydrochloride, showing almost the same changes in the intraocular pressure with the control group. The similar shift was found in the eye instilled with 0.1% nicardipine hydrochloride as with iganidipine hydrochloride, showing significant inhibition of the rise of intraocular pressure. In any eye instilled with physiological saline, which is the opposite eye from the eye instilled with the test material (the eye group instilled with each test material of non-treated eyes), inhibition of the rise of the intraocular pressure was found, as was the case with the eyes treated with test materials. Different from the eye instilled with test material, however, the intraocular pressure of the eye instilled with physiological saline restored to the original level in 60 minutes after laser irradiation, and the intraocular pressure decreased beyond the control group, and in 3 hours after irradiation, the eye instilled with iganidipine hydrochloride showed more significant decrease than did the intraocular pressure of the control group. From these results, the inventive compound was found to be useful.as an inhibitor of intraocular pressure rise after laser irradiation.

Formulation Example 1

| | |
|---|---|
| iganidipine hydrochloride | 0.1, 0.05 g |
| sodium acetate | 0.1 g |
| sodium chloride | 0.9 g |
| benzalkonium chloride | 0.005 g |
| acetic acid | appropriate amount |
| distilled water | total amount 100 ml |
| | pH 5.0 |

The above-mentioned ingredients are mixed by a conventional method to give an eye drop.

Formulation Example 2

| | |
|---|---|
| iganidipine hydrochloride | 0.1 g |
| liquid paraffin | 10 g |
| sterile purified water | appropriate amount |
| | total amount 100 g |

The above-mentioned ingredients are mixed by a conventional method to give an eye ointment.

INDUSTRIAL APPLICABILITY

The 1,4-dihydropyridine derivative (I) and an acid addition salt thereof contained in the preparation of the present invention are superior in water solubility and exhibit a superior anti-inflammatory effect and an inhibitory effect on the rise of intraocular pressure due to laser irradiation. Particularly, by topical administration to the eye of the inventive compound, a superior intraocular inflammation inhibitory effect and an inhibitory effect on the rise of intraocular pressure during operation with laser irradiation can be beneficially afforded.

This application is based on application No. 22249/1999 filed in Japan, the contents of which are incorporated hereinto by reference.

What is claimed is:

1. A method for prophylaxis or treatment of intraocular inflammation, which method comprises administering an effective amount of a 1,4-dihydropyridine compound of formula (1)

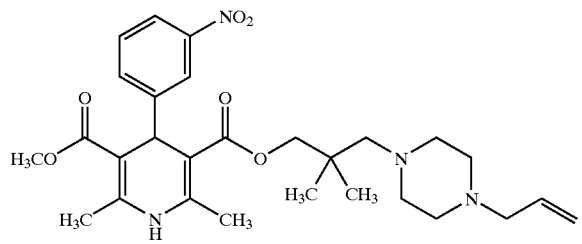

(I)

or an acid addition salt thereof, to a local site of the eye.

2. The method of claim 1, wherein the acid addition salt of the 1,4-dihydropyridine compound of the formula (I) is 3-(4-allyl-1-piperazinyl)-2,2-dimethylpropyl methyl 2,6-dimethyl-4-(m-nitrophenyl)-1,4-dihydropyridine-3,5-dicarboxylate dihydrochloride.

3. The method of claim 1, wherein the intraocular inflammation is caused by laser irradiation.

4. The method of claim 1, wherein the 1,4-dihydropyridine compound of the formula (1) or the acid addition salt thereof is administered in the form of an eye drop.

5. The method of claim 1, wherein the 1,4-dihydropyridine compound of the formula (I) or the acid addition salt thereof is administered in the form of an eye ointment.

6. A method of inhibiting rise of intraocular pressure due to laser irradiation, which method comprises administering an effective amount of a 1,4-dihydropyridine compound of formula (I)

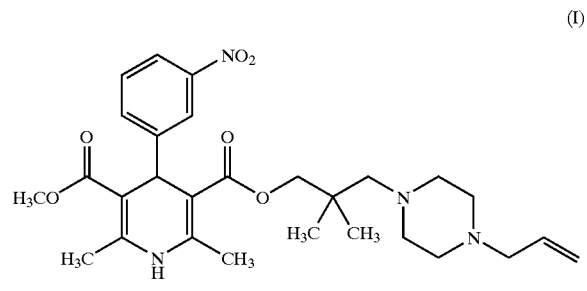

(I)

or an acid addition salt thereof, to a local site of the eye.

7. The method of claim 6, wherein the acid addition salt of the 1,4-dihydropyridine compound of the formula (I) is 3-(4-allyl-1-piperazinyl)-2,2-dimethylpropyl methyl 2,6-dimethyl-4-(m-nitrophenyl)-1,4-dihydropyridine-3,5-dicarboxylate dihydrochloride.

8. The method of claim 6, wherein the 1,4-dihydropyridine compound of the formula (I) or the acid addition salt thereof is administered in the form of an eye drop.

9. The method of claim 6, wherein the 1,4-dihydropyridine compound of the formula (I) or the acid addition salt thereof is administered in the form of an eye ointment.

* * * * *